United States Patent [19]

Takase et al.

[11] Patent Number: 5,112,833
[45] Date of Patent: May 12, 1992

[54] 1-AZAINDOLIZINE DERIVATIVES, SYNTHETIC INTERMEDIATES THEREOF AND ANTIALLERGIC AGENTS CONTAINING 1-AZAINDOLIZINE DERIVATIVES

[75] Inventors: Muneaki Takase, Tokyo; Toshihiko Komatsu, Saitama; Toshiyuki Matsuno, Saitama; Akihisa Miyakawa, Saitama; Kenichi Saito, Saitama, all of Japan

[73] Assignee: Zenyaku Kogyo Kabushiki Kaisha, Tokyo, Japan

[21] Appl. No.: 688,569

[22] PCT Filed: Dec. 26, 1989

[86] PCT No.: PCT/JP89/01302
§ 371 Date: Jun. 26, 1991
§ 102(e) Date: Jun. 26, 1991

[87] PCT Pub. No.: WO90/07508
PCT Pub. Date: Jul. 12, 1990

[30] Foreign Application Priority Data

Dec. 26, 1988 [JP] Japan .................. 63-328669

[51] Int. Cl.$^5$ .................. A61K 31/435; C07D 471/04
[52] U.S. Cl. .................................... 514/300; 546/121
[58] Field of Search .......................... 546/121; 514/300

[56] References Cited

FOREIGN PATENT DOCUMENTS 58-201780 11/1983 Japan .

OTHER PUBLICATIONS

Kurata et al., Yakugaku Zasshi, 101 (11), pp. 980-990 (1981).

Primary Examiner—Bernard Dentz
Attorney, Agent, or Firm—Oblon, Spivak, McClelland, Maier & Neustadt

[57] ABSTRACT

Novel 1-azaindolizine derivatives having excellent antiallergic action, synthetic intermediates thereof and antiallergic agents containing 1-azaindolizine derivatives.

9 Claims, No Drawings

1

1-AZAINDOLIZINE DERIVATIVES, SYNTHETIC INTERMEDIATES THEREOF AND ANTIALLERGIC AGENTS CONTAINING 1-AZAINDOLIZINE DERIVATIVES

TECHNICAL FIELD

The present invention relates to novel 1-azaindolizine (i.e., imidazo[1,2-a]pyridine) derivatives or pharmaceutically acceptable salts thereof, synthetic intermediates thereof and antiallergic agents containing 1-azaindolizine derivatives.

BACKGROUND ART

Several 1-azaindolizine derivatives have been already reported, but the derivatives having oxy and vinyl groups at positions 2 and 3, respectively, are disclosed only in Yakugaku Zasshi, 101, 11, pp. 980–990 (1981), Kurata et al, which has no pharmaceutical data. In recently increasing allergic diseases, rhinitis, bronchial asthma and others, patients are mainly treated with agents, such as disodium chromoglycate (DSCG) or tranilast, which inhibit the release of chemical mediators.

However, these agents do not exhibit sufficient effects against these disease and it is desired to develop a new antiallergic agent having more excellent activity.

Under these circumstances, we, the inventors carried out studies to find that the below-mentioned 1-azaindolizine derivatives of formula (I) exhibits remarkably excellent antiallergic activity, thus completing the present invention.

More specifically, 1-azaindolizine derivatives according to the present invention (hereinafter referred to as compounds of the present invention) are compounds or pharmaceutically acceptable salts thereof represented by formula (I)

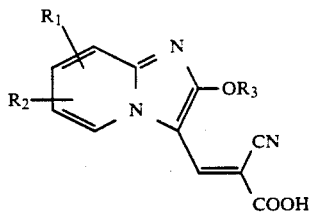
(I)

wherein $R_1$ and $R_2$ represent independently hydrogen atom, halogen atom, $C_{1-4}$ alkyl group or $C_{1-4}$ alkoxy group; and $R_3$ represents $C_{1-6}$ alkyl group, substituted $C_{1-4}$ alkyl group (substituent is $C_{3-5}$ cycloalkyl group, hydroxyl group, acetylamino group, $C_{1-4}$ alkoxy group or cyano group) or $C_{2-4}$ alkenyl group.

Synthetic intermediates of the compound (I) according to the present invention (hereinafter referred to as synthetic intermediates of the present invention) are represented by formula (II)

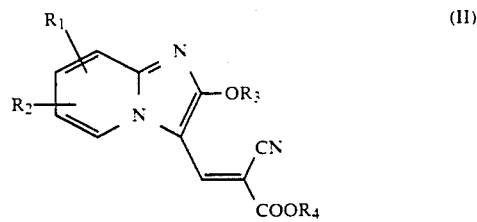
(II)

wherein $R_1$, $R_2$ and $R_3$ are as defined above and $R_4$ represents $C_{1-10}$ alkyl group or benzyl group.

Antiallergic agents of the present invention are agents containing the compound of the present invention as effective component.

The terms used for definition of letters in the formulas (I) and (II) by which the compounds of the present invention and synthetic intermediates thereof are respectively represented are defined and exemplified in the following.

The "halogen atom" may be chlorine, bromine or iodine atom.

The "$C_{1-4}$ alkyl group" refers to a straight- or branched-chain alkyl group having 1 to 4 carbon atoms such as methyl, ethyl, propyl, isopropyl, butyl, isobutyl, sec-butyl, tert-butyl or the like.

The "$C_{1-6}$ alkyl group" refers to a straight- or branched-chain alkyl group having 1 to 6 carbon atoms such as those referred to in the above-mentioned $C_{1-4}$ alkyl group, pentyl, hexyl or the like.

The "$C_{1-10}$ alkyl group" refers to a straight- or branched-chain alkyl group having 1 to 10 carbon atoms such as those referred to in the above-mentioned $C_{1-6}$ alkyl group, octyl, decyl or the like.

The "$C_{3-5}$ cycloalkyl group" refers to a cycloalkyl group having 3 to 5 carbon atoms such as cyclopropyl, cyclobutyl, cyclopentyl or the like.

The "$C_{1-4}$ alkoxy group" refers to a straight- or branched-chain alkoxy group having 1 to 4 carbon atoms such as methoxy, ethoxy, propoxy, isopropoxy, butoxy, isobutoxy, sec-butoxy, tert-butoxy or the like.

The "$C_{2-4}$ alkenyl group" refers to an alkenyl group having 2 to 4 carbon atoms such as vinyl, 1-propenyl, 2-propenyl, 2-butenyl, 3-butenyl or the like.

The compounds of the present invention are for example as follows:
3-(2-Carboxy-2-cyanovinyl)-2-methoxyimidazo[1,2-a]pyridine and its sodium salt
3-(2-Carboxy-2-cyanovinyl)-2-methoxy-5-methylimidazo[1,2-a]pyridine and its sodium salt
3-(2-Carboxy-2-cyanovinyl)-2-methoxy-6-methylimidazo[1,2-a]pyridine and its sodium salt
3-(2-Carboxy-2-cyanovinyl)-2-methoxy-7-methylimidazo[1,2-a]pyridine and its sodium salt
3-(2-Carboxy-2-cyanovinyl)-2-methoxy-8-methylimidazo[1,2-a]pyridine and its sodium salt
3-(2-Carboxy-2-cyanovinyl)-2-methoxy-5,7-dimethylimidazo[1,2-a]pyridine and its sodium salt
3-(2-Carboxy-2-cyanovinyl)-6,8-dichloro-2-methoxyimidazo[1,2-a]pyridine and its sodium salt
3-(2-Carboxy-2-cyanovinyl)-2,8-dimethoxyimidazo[1,2-a]pyridine and its sodium salt
3-(2-Carboxy-2-cyanovinyl)-8-isopropoxy-2-methoxyimidazo[1,2-a]pyridine and its sodium salt
3-(2-Carboxy-2-cyanovinyl)-2-ethoxy-8-methylimidazo[1,2-a]pyridine and its sodium salt 3-(2-Carboxy-2-cyanovinyl)-2-ethoxy-8-isopropoxyimidazo[1,2-a]pyridine and its sodium salt
3-(2-Carboxy-2-cyanovinyl)-8-methyl-2-propoxyimidazo[1,2-a]pyridine and its sodium salt
3-(2-Carboxy-2-cyanovinyl)-2-isopropoxy-6-methylimidazo[1,2-a]pyridine and its sodium salt
3-(2-Carboxy-2-cyanovinyl)-2-isopropoxy-7-methylimidazo[1,2-a]pyridine and its sodium salt
3-(2-Carboxy-2-cyanovinyl)-2-isopropoxy-8-methylimidazo[1,2-a]pyridine and its sodium salt
3-(2-Carboxy-2-cyanovinyl)-6,8-dichloro-2-isopropoxyimidazo[1,2-a]pyridine and its sodium salt
3-(2-Carboxy-2-cyanovinyl)-2-isopropoxy-8-methoxyimidazo[1,2-a]-pyridine and its sodium salt
3-(2-Carboxy-2-cyanovinyl)-8-ethoxy-2-isopropoxyimidazo[1,2-a]-pyridine and its sodium salt
3-(2-Carboxy-2-cyanovinyl)-2,8-diisopropoxyimidazo[1,2-a]pyridine and its sodium salt
2-Butoxy-3-(2-carboxy-2-cyanovinyl)-8-methylimidazo[1,2-a]-pyridine and its sodium salt
2-Butoxy-3-(2-carboxy-2-cyanovinyl)-8-isopropoxyimidazo[1,2-a]pyridine and its sodium salt
3-(2-Carboxy-2-cyanovinyl)-2-isobutoxy-5-methylimidazo[1,2-a]pyridine and its sodium salt
3-(2-Carboxy-2-cyanovinyl)-2-isobutoxy-6-methylimidazo[1,2-a]pyridine and its sodium salt
3-(2-Carboxy-2-cyanovinyl)-2-isobutoxy-7-methylimidazo[1,2-a]pyridine and its sodium salt
3-(2-Carboxy-2-cyanovinyl)-2-isobutoxy-8-methylimidazo[1,2-a]pyridine and its sodium salt
3-(2-Carboxy-2-cyanovinyl)-8-ethoxy-2-isobutoxyimidazo[1,2-a]pyridine and its sodium salt
3-(2-Carboxy-2-cyanovinyl)-2-isobutoxy-8-isopropoxyimidazo[1,2-a]pyridine and its sodium salt
3-(2-Carboxy-2-cyanovinyl)-8-methyl-2-sec-butoxyimidazo[1,2-a]pyridine and its sodium salt
3-(2-Carboxy-2-cyanovinyl)-8-ethoxy-2-sec-butoxyimidazo[1,2-a]pyridine and its sodium salt
3-(2-Carboxy-2-cyanovinyl)-8-isopropoxy-2-sec-butoxyimidazo[1,2-a]pyridine and its sodium salt
3-(2-Carboxy-2-cyanovinyl)-8-methyl-2-tert-butoxyimidazo[1,2-a]pyridine and its sodium salt
3-(2-Carboxy-2-cyanovinyl)-8-isopropoxy-2-tert-butoxyimidazo[1,2-a]pyridine and its sodium salt
3-(2-Carboxy-2-cyanovinyl)-8-methyl-2-pentyloxyimidazo[1,2-a]pyridine and its sodium salt
3-(2-Carboxy-2-cyanovinyl)-6,8-dichloro-2-pentyloxyimidazo[1,2-a]pyridine and its sodium salt
3-(2-Carboxy-2-cyanovinyl)-8-isopropoxy-2-pentyloxyimidazo[1,2-a]pyridine and its sodium salt
3-(2-carboxy-2-cyanovinyl)-2-hexyloxy-8-methylimidazo[1,2-a]pyridine and its sodium salt
3-(2-Carboxy-2-cyanovinyl)-2-hexyloxy-8-isopropoxyimidazo[1,2-a]pyridine and its sodium salt
3-(2-Carboxy-2-cyanovinyl)-8-methyl-2-vinyloxyimidazo[1,2-a]pyridine and its sodium salt
3-(2-Carboxy-2-cyanovinyl)-8-isopropoxy-2-vinyloxyimidazo[1,2-a]pyridine and its sodium salt
3-(2-Carboxy-2-cyanovinyl)-8-methyl-2-(2-propenyloxy)imidazo[1,2-a]pyridine and its sodium salt
3-(2-Carboxy-2-cyanovinyl)-8-isopropoxy-2-(2-propenyloxy)imidazo[1,2-a]pyridine and its sodium salt
2-(3-Butenyloxy)-3-(2-carboxy-2-cyanovinyl)-8-methylimidazo[1,2-a]pyridine and its sodium salt
2-(3-Butenyloxy)-3-(2-carboxy-2-cyanovinyl)-8-isopropoxyimidazo[1,2-a]pyridine and its sodium salt
3-(2-Carboxy-2-cyanovinyl)-2-(3-hydroxypropoxy)-8-methylimidazo[1,2-a]pyridine and its sodium salt
3-(2-Carboxy-2-cyanovinyl)-2-(2-hydroxyethoxy)-8-methylimidazo[1,2-a]pyridine and its sodium salt
2-(3-Acetylaminopropoxy)-3-(2-carboxy-2-cyanovinyl)-8-methylimidazo[1,2-a]pyridine and its sodium salt
3-(2-Carboxy-2-cyanovinyl)-2-cyclopropylmethoxy-8-methylimidazo[1,2-a]pyridine and its sodium salt
3-(2-Carboxy-2-cyanovinyl)-2-(2-methoxyethoxy)-8-methylimidazo[1,2-a]pyridine and its sodium salt
3-(2-Carboxy-2-cyanovinyl)-2-(2-ethoxyethoxy)-8-methylimidazo[1,2-a]pyridine and its sodium salt
3-(2-Carboxy-2-cyanovinyl)-2-(3-cyanopropoxy)-8-methylimidazo[1,2-a]pyridine and its sodium salt Pharmaceutically acceptable salts of the compounds of the present invention may be potassium salt and calcium salt as well as the above-mentioned sodium salt.

Synthetic intermediates of the present invention correspond to $C_{1-10}$ alkyl esters or benzyl esters of the compounds of the present invention and may be for example as follows:

3-[2-Cyano-2-(ethoxycarbonyl)vinyl]-2-methoxyimidazo[1,2-a]pyridine
3-[2-Cyano-2-(ethoxycarbonyl)vinyl]-2-methoxy-5-methylimidazo[1,2-a]pyridine
3-[2-Cyano-2-(ethoxycarbonyl)vinyl]-2-methoxy-6-methylimidazo[1,2-a]pyridine
3-[2-Cyano-2-(ethoxycarbonyl)vinyl]-2-methoxy-7-methylimidazo[1,2-a]pyridine
3-[2-Cyano-2-(ethoxycarbonyl)vinyl]-2-methoxy-8-methylimidazo[1,2-a]pyridine
3-[2-(Benzyloxycarbonyl)-2-cyanovinyl]-2-methoxy-5,7-dimethylimidazo[1,2-a]pyridine
3-[2-(Benzyloxycarbonyl)-2-cyanovinyl]-6,8-dichloro-2-methoxyimidazo[1,2-a]pyridine
3-[2-(Benzyloxycarbonyl)-2-cyanovinyl]-2,8-dimethoxyimidazo[1,2-a]pyridine
3-[2-(Benzyloxycarbonyl)-2-cyanovinyl]-8-isopropoxy-2-methoxyimidazo[1,2-a]pyridine
3-[2-(Benzyloxycarbonyl)-2-cyanovinyl]-2-ethoxy-8-methylimidazo[1,2-a]pyridine
3-[2-(Benzyloxycarbonyl)-2-cyanovinyl]-2-ethoxy-8-isopropoxyimidazo[1,2-a]pyridine
3-[2-(Benzyloxycarbonyl)-2-cyanovinyl]-8-methyl-2-propoxyimidazo[1,2-a]pyridine
3-[2-(Benzyloxycarbonyl)-2-cyanovinyl]-2-isopropoxy-6-methylimidazo[1,2-a]pyridine
3-[2-(Benzyloxycarbonyl)-2-cyanovinyl]-2-isopropoxy-7-methylimidazo[1,2-a]pyridine
3-[2-(Benzyloxycarbonyl)-2-cyanovinyl]-2-isopropoxy-8-methylimidazo[1,2-a]pyridine
3-[2-(Benzyloxycarbonyl)-2-cyanovinyl]-6,8-dichloro-2-isopropoxyimidazo[1,2-a]pyridine
3-[2-(Benzyloxycarbonyl)-2-cyanovinyl]-2-isopropoxy-8-methoxyimidazo[1,2-a]pyridine
3-[2-(Benzyloxycarbonyl)-2-cyanovinyl]-8-ethoxy-2-isopropoxyimidazo[1,2-a]pyridine
3-[2-(Benzyloxycarbonyl)-2-cyanovinyl]-2,8-diisopropoxyimidazo[1,2-a]pyridine
3-[2-Cyano-2-(ethoxycarbonyl)vinyl]-2,8-diisopropoxyimidazo[1,2-a]pyridine
3-[2-Cyano-2-(isopentyloxycarbonyl)vinyl]-2,8-diisopropoxyimidazo[1,2-a]pyridine
3-[2-Cyano-2-(n-decyloxycarbonyl)vinyl]-2,8-diisopropoxyimidazo[1,2-a]pyridine
3-[2-(Benzyloxycarbonyl)-2-cyanovinyl]-2-butoxy-8-methylimidazo[1,2-a]pyridine 3-[2-(Benzyloxycarbonyl)-2-cyanovinyl]-2-butoxy-8-isopropoxyimidazo[1,2-a]pyridine
3-[2-(Benzyloxycarbonyl)-2-cyanovinyl]-2-isobutoxy-5-methylimidazo[1,2-a]pyridine
3-[2-(Benzyloxycarbonyl)-2-cyanovinyl]-2-isobutoxy-6-methylimidazo[1,2-a]pyridine
3-[2-(Benzyloxycarbonyl)-2-cyanovinyl]-2-isobutoxy-7-methylimidazo[1,2-a]pyridine
3-[2-(Benzyloxycarbonyl)-2-cyanovinyl]-2-isobutoxy-8-methylimidazo[1,2-a]pyridine
3-[2-(Benzyloxycarbonyl)-2-cyanovinyl]-8-ethoxy-2-isobutoxyimidazo[1,2-a]pyridine
3-[2-(Benzyloxycarbonyl)-2-cyanovinyl]-2-isobutoxy-8-isopropoxyimidazo[1,2-a]pyridine
3-[2-(Benzyloxycarbonyl)-2-cyanovinyl]-8-methyl-2-sec-butoxyimidazo[1,2-a]pyridine
3-[2-(Benzyloxycarbonyl)-2-cyanovinyl]-8-ethoxy-2-sec-butoxyimidazo[1,2-a]pyridine
3-[2-(Benzyloxycarbonyl)-2-cyanovinyl]-8-isopropoxy-2-sec-butoxyimidazo[1,2-a]pyridine
3-[2-(Benzyloxycarbonyl)-2-cyanovinyl]-8-methyl-2-tert-butoxyimidazo[1,2-a]pyridine
3-[2-(Benzyloxycarbonyl)-2-cyanovinyl]-8-isopropoxy-2-tert-butoxyimidazo[1,2-a]pyridine
3-[2-(Benzyloxycarbonyl)-2-cyanovinyl]-8-methyl-2-pentyloxyimidazo[1,2-a]pyridine
3-[2-(Benzyloxycarbonyl)-2-cyanovinyl]-6,8-dichloro-2-pentyloxyimidazo[1,2-a]pyridine
3-[2-(Benzyloxycarbonyl)-2-cyanovinyl]-8-isopropoxy-2-pentyloxyimidazo[1,2-a]pyridine
3-[2-(Benzyloxycarbonyl)-2-cyanovinyl]-2-hexyloxy-8-methylimidazo[1,2-a]pyridine
3-[2-(Benzyloxycarbonyl)-2-cyanovinyl]-2-hexyloxy-8-isopropoxyimidazo[1,2-a]pyridine
3-[2-Cyano-2-(ethoxycarbonyl)vinyl]-8-methyl-2-vinyloxyimidazo[1,2-a]pyridine
3-[2-Cyano-2-(ethoxycarbonyl)vinyl]-8-isopropoxy-2-vinyloxyimidazo[1,2-a]pyridine
3-[2-Cyano-2-(ethoxycarbonyl)vinyl]-8-methyl-2-(2-propenyloxy)imidazo[1,2-a]pyridine
3-[2-Cyano-2-(ethoxycarbonyl)vinyl]-8-isopropoxy-2-(2-propenyloxy)imidazo[1,2-a]pyridine
2-(3-Butenyloxy)-3-[2-cyano-2-(ethoxycarbonyl)vinyl]-8-methylimidazo[1,2-a]pyridine
2-(3-Butenyloxy)-3-[2-cyano-2-(ethoxycarbonyl)vinyl]-8-isopropoxyimidazo[1,2-a]pyridine
3-[2-(Benzyloxycarbonyl)-2-cyanovinyl]-2-(2-hydroxyethoxy)-8-methylimidazo[1,2-a]pyridine
3-[2-(Benzyloxycarbonyl)-2-cyanovinyl]-2-(3-hydroxypropoxy)-8-methylimidazo[1,2-a]pyridine
2-[3-(Acetylaminopropoxy)-3-[2-(benzyloxycarbonyl)-2-cyanovinyl]-8methylimidazo[1,2-a]pyridine
3-[2-(Benzyloxycarbonyl)-2-cyanovinyl]-2-cyclopropylmethoxy-8-methylimidazo[1,2-a]pyridine
3-[2-(Benzyloxycarbonyl)-2-cyanovinyl]-2-(2-methoxyethoxy)-8-methylimidazo[1,2-a]pyridine
3-[2-(Benzyloxycarbonyl)-2-cyanovinyl]-2-(2-ethoxyethoxy)-8-methylimidazo[1,2-a]pyridine
3-[2-(Benzyloxycarbonyl)-2-cyanovinyl]-2-(3-cyanopropoxy)-8-methylimidazo[1,2-a]pyridine The compounds of the present invention can be readily prepared by catalytic hydrogenation or alkaline hydrolysis of the above-mentioned intermediates followed by convertment to the pharmaceutically acceptable salts thereof.

In the case of the catalytic hydrogenation, 10% palladium on carbon, 5% palladium on barium sulfate, platinum oxide may be used as a catalyst; 10% palladium on carbon is preferable. The amount of the catalyst used in the hydrogenation is usually within the range from 0.01% to 0.05% of weight of the intermediates. As for the reaction solvent, methanol, ethanol, acetic acid or dioxane may be used; ethanol is preferable. The reaction temperature may range from 0° to 80° C., preferably within at room temperature. The reaction time may range from 1 to 24 hours which depends on reaction temperature.

In the case of alkaline hydrolysis, alkali used may be potassium hydroxide, sodium hydroxide, sodium carbonate, potassium carbonate, sodium hydrogencarbonate. As the reaction solvent, water, methanol, ethanol or their mixture may be used. The reaction temperature may range from 0° to 80° C., preferably from 50° to 70° C., and the reaction time may range from 0.5 to 24 hours, preferably from 0.5 to 2 hours, which depends on reaction temperature.

The compounds (carboxylic acids) obtained by the above-mentioned catalytic hydrogenation or alkaline hydrolysis may be converted to pharmaceutically acceptable salts thereof such as sodium salt, potassium salt or calcium salt in a usual manner; alternatively, said obtained compound may be converted to salts thereof without isolation.

Thus obtained compound of the present invention or pharmaceutically acceptable salts thereof may be isolated by usual separating and purifying manners such as extraction, concentration, neutralization, filtration, recrystallization or column chromatography. The intermediates of the present invention are also novel compounds and are prepared by a similar method described in Chemical & Pharmaceutical Bulletin, 34, 6, 2435~2442(1986) Kakei et al and Yakugaku Zasshi, 101, 11, 980~990(1981) Kurata et al. More specifically, the intermediate of the present invention is readily prepared as shown in the scheme. Pyridinium bromide of below-mentioned formula (III) is reacted with the compound of below-mentioned formula (IV) in the presence of base such as 1,8-diazabicyclo[5,4,0]-7-undecene, 1,5-diazabicyclo[4,3,0]-5-nonen, sodium ethoxide, sodium methoxide or potassium tert-butoxide and then is reacted to the compound with the formula (V).

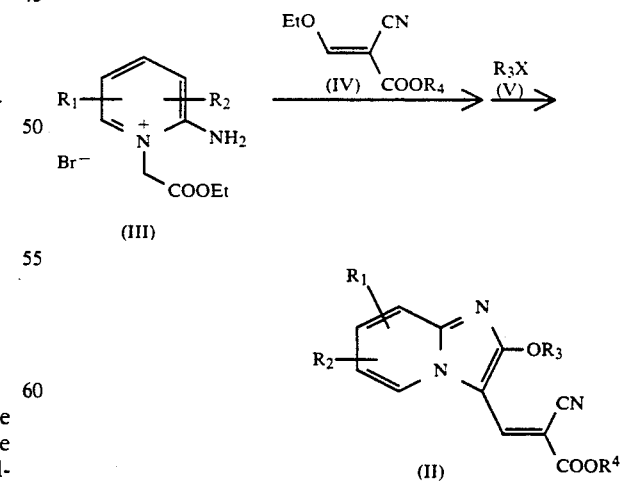

wherein $R_1$, $R_2$, $R_3$ and $R_4$ are as defined above and X represents halogen.

The synthetic intermediate of the present invention itself has antiallergic activities.

The antiallergic action of the compounds of the present invention obtained by the above-mentioned preparation process was examining by the following inhibition test of homologous passive cutaneous anaphylaxis (PCA) reaction on rats.

Numbers and names of samples used in the test were as follows:

Sample 1: Sodium salt of 3-(2-carboxy-2-cyanovinyl)-2-methoxy-6-methylimidazo[1,2-a]pyridine
Sample 2: Sodium salt of 3-(2-carboxy-2-cyanovinyl)-2-isopropoxy-8-methylimidazo[1,2-a]pyridine
Sample 3: Sodium salt of 3-(2-carboxy-2-cyanovinyl)-2-isopropoxy-8-methoxyimidazo[1,2-a]pyridine
Sample 4: Sodium salt of 3-(2-carboxy-2-cyanovinyl)-8-ethoxy-2-isopropoxyimidazo[1,2-a]pyridine
Sample 5: Sodium salt of 3-(2-carboxy-2-cyanovinyl)-2,8-diisopropoxyimidazo[1,2-a]pyridine
Sample 6: Sodium salt of 2-butoxy-3-(2-carboxy-2-cyanovinyl)-8-methylimidazo[1,2-a]pyridine
Sample 7: Sodium salt of 3-(2-carboxy-2-cyanovinyl)-2-isobutoxy-7-methylimidazo[1,2-a]pyridine
Sample 8: Sodium salt of 3-(2-carboxy-2-cyanovinyl)-8-methyl-2-secbutoxyimidazo[1,2-a]pyridine
Sample 9: Sodium salt of 3-(2-carboxy-2-cyanovinyl)-8-ethoxy-2-secbutoxyimidazo[1,2-a]pyridine
Sample 10: Sodium salt of 3-(2-carboxy-2-cyanovinyl)-8-isopropoxy-2-secbutoxyimidazo[1,2-a]pyridine
Sample 11: Sodium salt of 3-(2-carboxy-2-cyanovinyl)-2-hexyloxy-8-methylimidazo[1,2-a]pyridine
Sample 12: Sodium salt of 2-(3-butenyloxy)-3-(2-carboxy-2-cyanovinyl)-8-methylimidazo[1,2-a]pyridine
Sample 13: Sodium salt of 3-(2-carboxy-2-cyanovinyl)-2-(3-hydroxypropoxy)-8-methylimidazo[1,2-a]pyridine
Sample 14: Sodium salt of 2-(3-acetylaminoproxy)-3-(2-carboxy-2-cyanovinyl)-8-methylimidazo[1,2-a]pyridine
Sample 15: Sodium salt of 3-(2-carboxy-2-cyanovinyl)-2-cyclopropylmethoxy-8-methylimidazo[1,2-a]pyridine
Sample 16: Sodium salt of 3-(2-carboxy-2-cyanovinyl)-2-(2-methoxyethoxy)-8-methylimidazo[1,2-a]pyridine
Sample 17: Sodium salt of 3-(2-carboxy-2-cyanovinyl)-2-(3-cyanoproxy)-8-methylimidazo[1,2-a]pyridine 1: Inhibition of homologous passive cutaneous anaphylaxis (PCA) reaction Antiserum was obtained from rats that were immunized with ovalbumin according to the method of Mota [Immunology, 7, 681-699 (1964)]. The antiserum was diluted with physiological saline to make PCA reaction of approximately 10-15 mm in diameter. Groups of 5 male Wistar rats, 8 weeks old and weighing between 200-250 g, were passively sensitized with 0.1 ml of the diluted antiserum injected intradermally in the shaved area on the back. Fourty-eight hours after the sensitization, each above sample dissolved into physiological saline was injected into the rats intravenously via tail vein. Immediately after injection of the sample, rats were challenged with the physiological saline solution containing ovalbumin (25 mg/kg/head) and Evans blue (12.5 mg/kg/head) intravenously via tail vein so as to generate PCA reaction. Thirty minutes after the accomplishment of the challenge, the rats were exsanguinated and removed the skins from the back. The amount of the dye leaked out of the vessels was measured by the method of Katayama et al. [Microbiol. Immunol. 22, 89-101 (1978)].

The effects of samples on PCA reaction were expressed as percentage of inhibition of the leaked amount of the dye calculated by the following equation:

$$\text{Inhibition } (\%) = \frac{C - S}{C} \times 100$$

where C is the mean leaked amount of the dye in control group, S is the mean leaked amount of dye in sample treated group. The results of the experiments were shown in Table 1, which included the effect of DSCG used as a positive control.

TABLE 1

| Sample No. | Dose (mg/kg) | Inhibition (%) |
|---|---|---|
| 1 | 20 | 52.6* |
| 2 | 20 | 68.4** |
| 3 | 20 | 90.0** |
| 4 | 20 | 85.4** |
| 5 | 20 | 94.6** |
| 6 | 20 | 69.8** |
| 7 | 20 | 65.8** |
| 8 | 20 | 80.4** |
| 9 | 20 | 75.3** |
| 10 | 20 | 92.5** |
| 11 | 20 | 75.7** |
| 12 | 20 | 68.9** |
| 13 | 20 | 64.3** |
| 14 | 20 | 74.8** |
| 15 | 20 | 61.8** |
| 16 | 20 | 68.9** |
| 17 | 20 | 71.3** |
| (DSCG) | 10 | 75.0** |

*$P < 0.02$
**$P < 0.005$

The evidences that the compounds of the present invention revealed an excellent inhibition against PCA reaction indicated the possibility of these compounds to be a remedy or a prophylactic for allergic disorders such as allergic bronchial asthma, allergic rhinitis and atopic dermatitis.

Acute toxicity tests of the compounds of the present invention were carried out as described below. Groups of 5 male ICR mice, 5 weeks old and weighing 30±5 g, were used. The samples dissolved in physiological saline were injected intravenously via tail vein of the mice. Each $LD_{50}$ was determined through 10 days' observation.

The typical results are as shown in Table 2.

TABLE 2

| Sample No.[a] | Acute Toxicity $LD_{50}$ (mg/kg) |
|---|---|
| 2 | ca. 150 |
| 3 | ca. 350 |
| 5 | ca. 220 |

[a]Sample numbers shown are the same as those in the test for PCA reaction inhibition.

The following descriptions are given for the administration routes, pharmaceutical forms and doses when the compounds of the present invention are applied as antiallergic agent to human.

The compounds of the present invention may be administered orally in forms such as tablets, coated tablets, powders, granules, capsules, microcapsules, syrups and so on. They may be also administered parenterally in forms such as liquids, ointments, creams, gels, poultices, injections including freeze-dried products which are to be dissolved upon use, suppositories and so on. These preparations may be prepared using pharmaceutically acceptable excipients, binders, lubricants, disintegrators, suspensions, emulsifiers, antiseptics, stabilizers or dispersing agents such as lactose, sucrose, starch, dextrin, crystalline cellulose, kaolin, calcium carbonate, talc, magnesium stearate, distilled water or physiological saline solution.

Although the daily doses of these compounds may be varied according to the conditions, ages or weights of the subjects to be treated, the daily doses to adult humans may normally fall within the range of 1~300 mg, preferably 50~200 mg, and may be divided into two or three portions.

BEST MODE FOR CARRYING OUT THE INVENTION

The present invention is more specifically illustrated with reference to the following examples. It is to be, however, noted that the present invention is not limited to the examples.

EXAMPLE 1

3-[2-Cyano-2-(ethoxycarbonyl)vinyl]-2-methoxy-8-methylimidazo[1,2-a]pyridine

Eight ml of 1,8-diazabicyclo[5,4,0]-7-undecene was added dropwise to a mixture of 2-amino-1-(ethoxycarbonylmethyl)-3-methylpyridinium bromide (5.5 g; 20 mmol) and dichloromethane (200 ml), and then the mixture was stirred for 30 min at room temperature. To the stirred mixture was dropped 1-cyano-1-(ethoxycarbonyl)-2-ethoxyethylene (3.4 g; 20 mmol) in dichloromethane (100 ml) and the mixture was further stirred for 30 min at room temperature. The mixture was evaporated, and the resultant residue was dissolved in 200 ml of acetone. Methyl iodide (20 ml; 32 mmol) was added to the acetone solution and the solution was heated under reflux for 1.5 hour at 60° C. After standing for several hours at room temperature, the resultant precipitates were removed by filtration. The filtrate was concentrated, and the residue was dissolved in dichloromethane, the solution was washed with water, dried over anhydrous magnesium sulfate, successively. The residue, obtained by evaporating the solvent, was chromatographed over silicagel [eluant: hexane-ethyl acetate (2:1)] to give 3.12 g (yield: 55%) of the titled compound as yellow needles.

Melting Point: 127°~129° C.
IR Spectrum $\nu_{max}^{KBr}$cm$^{-1}$: 2220(C≡N), 1710(C=O)
NMR Spectrum (CDCl$_3$) δppm: 1.38 (3H, t, J=7 Hz) 2.56 (3H, s) 4.23 (3H, s) 4.35 (2H, q, J=7 Hz) 6.99 (1H, dd, J=7 Hz,7 Hz) 7.28 (1H, d, J=7 Hz) 8.23 (1H, s) 8.35 (1H, d, J=7 Hz)

In accordance with the procedure of the Example 1, the following compounds were obtained from the corresponding starting materials.

3-[2-Cyano-2-(ethoxycarbonyl)vinyl]-2-methoxyimidazo[1,2-a]pyridine
Melting Point: 134°~136° C.
IR Spectrum $\nu_{max}^{KBr}$cm$^{-1}$: 2220(C≡N), 1710(C=O)
NMR Spectrum (CDCl$_3$) δppm: 1.39 (3H, t, J=7 Hz) 4.22 (3H, s) 4.35 (2H, q, J=7 Hz) 7.10 (1H, dd, J=7 Hz,7 Hz) 7.50 (1H, dd, J=7 Hz,7 Hz) 7.53 (1H, d, J=7 Hz) 8.25 (1H, s) 8.52 (1H, d, J=7 Hz)

3-[2-Cyano-2-(ethoxycarbonyl)vinyl]-2-methoxy-6-methylimidazo[1,2-a]pyridine
Melting Point: 132.5°~133.5° C.

IR Spectrum $\nu_{max}^{KBr}$cm$^{-1}$: 2230(C≡N), 1710(C=O)
NMR Spectrum (CDCl$_3$) δppm: 1.39 (3H, t, J=7 Hz) 2.42 (3H, s) 4.20 (3H, s) 4.36 (2H, q, J=7 Hz) 7.34 (1H, d, J=9 Hz) 7.45 (1H, d, J=9 Hz) 8.22 (1H, s) 8.29 (1H, broad s)

3-[2-Cyano-2-(ethoxycarbonyl)vinyl]-8-methyl-2-(2-propenyloxy)imidazo[1,2-a]pyridine
Melting Point: 84°~85° C.
IR Spectrum $\nu_{max}^{KBr}$cm$^{-1}$: 2225(C≡N), 1695(C=O)
NMR Spectrum (CDCl$_3$) δppm: 1.38 (3H, t, J=7 Hz) 2.54 (3H, s) 4.35 (2H, q, J=7 Hz) 5.10 (2H, d, J=6 Hz) 5.2~5.4 (1H, m) 5.49 (1H, d, J=17 Hz) 6.1~6.3 (1H, m) 6.98 (1H, t, J=7 Hz) 7.31 (1H, d, J=7 Hz) 8.26 (1H, s) 8.37 (1H, d, J=7 Hz)

2-(3-Butenyloxy)-3-[2-cyano-2-(ethoxycarbonyl)vinyl]-8-methylimidazo[1,2-a]pyridine
Melting Point: 108°~109° C.
IR Spectrum $\nu_{max}^{KBr}$cm$^{-1}$: 2220(C≡N), 1695(C=O)
NMR Spectrum (CDCl$_3$) δppm: 1.38 (3H, t, J=7 Hz) 2.54 (3H, s) 2.70 (2H, q, J=7 Hz) 4.34 (2H, q, J=7 Hz) 4.63 (2H, t, J=7 Hz) 5.11 (1H, d, J=10 Hz) 5.20 (1H, d, J=17 Hz) 5.8~6.1 (1H, m) 6.97 (1H, t, J=7 Hz) 7.27 (1H, d, J=7 Hz) 8.22 (1H, s) 8.34 (1H, d, J=7 Hz)

EXAMPLE 2

3-[2-(Benzyloxycarbonyl)-2-cyanovinyl]-2-ethoxy-8-methylimidazo[1,2-a]pyridine

To a stirred sodium ethoxide solution, freshly prepared with 140 mg of sodium in 30 ml of absolute ethanol, was added 850 mg (3 mmol) of 2-amino-1-(ethoxycarbonylmethyl)-3-methylpyridinium bromide, then the mixture was stirred for 30 min at room temperature. The reaction mixture was treated with 1-(benzyloxycarbonyl)-1-cyano-2-ethoxyethylene (710 mg; 3 mmol) followed by stirred for 30 min at room temperature. The resultant precipitates were collected by filtration, dried, then dissolved in 8 ml of N,N-dimethylformamide (DMF). Ethyl iodide (0.32 ml; 4 mmol) was added to the DMF solution and the mixture was stirred for 2 hours at 60° C. The reaction mixture was cooled at room temperature, extracted with ethyl acetate, the solution was washed with water, dried over anhydrous magnesium sulfate, successively. After removal of the solvent, the residue was chromatographed over silicagel [eluant: n-hexane-ethyl acetate (1:1)] to give 470 mg (yield: 43%) of the titled compound as yellow needles.

Melting Point: 101.5°~103.5° C.
IR Spectrum $\nu_{max}^{KBr}$cm$^{-1}$: 2230(C≡N), 1705(C=O)
NMR Spectrum (CDCl$_3$) δppm: 1.54 (3H, t, J=7 Hz) 2.54 (3H, s) 4.65 (2H, q, J=7 Hz) 5.34 (2H, s) 6.97 (1H, t, J=7 Hz) 7.2~7.5 (6H, m) 8.24 (1H, s) 8.34 (1H, d, J=7 Hz)

In accordance with the procedure of the Example 2, the following compounds were obtained from the corresponding starting materials.

3-[2-(Benzyloxycarbonyl)-2-cyanovinyl]-2-methoxy-5,7-dimethylimidazo[1,2-a]pyridine
Melting Point: 156°~157° C.
IR Spectrum $\nu_{max}^{KBr}$cm$^{-1}$: 2200(C≡N), 1690(C=O)
NMR Spectrum (CDCl$_3$) δppm: 2.41 (3H, s) 2.81 (3H, s) 4.23 (3H, s) 5.32 (2H, s) 6.65 (1H, s) 7.21 (1H, s) 7.3~7.5 (5H, m) 8.62 (1H, s)

3-[2-(Benzyloxycarbonyl)-2-cyanovinyl]-6,8-dichloro-2-methoxyimidazo[1,2-a]pyridine
Melting Point: 154°~155° C.
IR Spectrum $\nu_{max}^{KBr}$ cm$^{-1}$: 2225(C≡N), 1695(C=O)
NMR Spectrum (CDCl$_3$) δppm: 4.27 (3H, s) 5.35 (2H, s) 7.3~7.5 (5H, m) 7.52 (1H, d, J=1 Hz) 8.18 (1H, s) 8.32 (1H, d, J=1 Hz)

3-[2-(Benzyloxycarbonyl)-2-cyanovinyl]-2-ethoxy-8-isopropoxyimidazo-[1,2-a]pyridine
Melting Point: 107°~108° C.
IR Spectrum $\nu_{max}^{KBr}$ cm$^{-1}$: 2215(C≡N), 1695(C=O)
NMR Spectrum (CDCl$_3$) δppm: 1.46 (6H, d, J=6 Hz) 1.53 (3H, t, J=7 Hz) 4.68 (2H, q, J=7 Hz) 4.85 (1H, m) 5.34 (2H, s) 6.86 (1H, d, J=7 Hz) 6.95 (1H, t, J=7 Hz) 7.3~7.5 (5H, m) 8.06 (1H, d, J=7 Hz) 8.24 (1H, s)

3-[2-(Benzyloxycarbonyl)-2-cyanovinyl]-8-methyl-2-propoxyimidazo[1,2-a]pyridine
Melting Point: 101°~103° C.
IR Spectrum $\nu_{max}^{KBr}$ cm$^{-1}$: 2210(C≡N), 1700(C=O)
NMR Spectrum (CDCl$_3$) δppm: 1.07 (3H, t, J=7 Hz) 1.95 (2H, m) 2.55 (3H, s) 4.55 (2H, t, J=7 Hz) 5.34 (2H, s) 6.97 (1H, t, J=7 Hz) 7.2~7.5 (6H, m) 8.25 (1H, s) 8.35 (1H, d, J=7 Hz)

3-[2-(Benzyloxycarbonyl)-2-cyanovinyl]-2-isopropoxy-8-methylimidazo[1,2-a]pyridine
Melting Point: 112.5°~114.5° C.
IR Spectrum $\nu_{max}^{KBr}$ cm$^{-1}$: 2240(C≡N), 1700(C=O)
NMR Spectrum (CDCl$_3$) δppm: 1.50 (6H, d, J=6 Hz) 2.54 (3H, s) 5.34 (2H, s) 5.47 (1H, m) 6.96 (1H, t, J=7 Hz) 7.2~7.5 (6H, m) 8.23 (1H, s) 8.35 (1H, d, J=7 Hz)

3-[2-(Benzyloxycarbonyl)-2-cyanovinyl]-2-isopropoxy-8-methoxyimidazo[1,2-a]pyridine
Melting Point: 122°~123° C.
IR Spectrum $\nu_{max}^{KBr}$ cm$^{-1}$: 2220(C≡N), 1710(C=O) NMR Spectrum (CDCl$_3$) δppm: 1.49 (6H, d, J=6 Hz) 4.04 (3H, s) 5.34 (2H, s) 5.55 (1H, m) 6.83 (1H, d, J=7 Hz) 6.96 (1H, t, J=7 Hz) 7.3~7.5 (5H, m) 8.08 (1H, d, J=7 Hz) 8.23 (1H, s)

3-[2-(Benzyloxycarbonyl)-2-cyanovinyl]-8-ethoxy-2-isopropoxyimidazo[1,2-a]pyridine
Melting Point: 101°~103° C.
IR Spectrum $\nu_{max}^{KBr}$ cm$^{-1}$: 2230(C≡N), 1700(C=O)
NMR Spectrum (CDCl$_3$) δppm: 1.50 (6H, d, J=6 Hz) 1.55 (3H, t, J=7 Hz) 4.33 (2H, q, J=7 Hz) 5.34 (2H, s) 5.45 (1H, m) 6.86 (1H, d, J=7 Hz) 6.97 (1H, t, J=7 Hz) 7.3~7.5 (5H, m) 8.16 (1H, d, J=7 Hz) 8.22 (1H, s)

3-[2-(Benzyloxycarbonyl)-2-cyanovinyl]-2,8-diisopropoxyimidazo[1,2-a]-pyridine
Melting Point: 114°~115° C.
IR Spectrum $\nu_{max}^{KBr}$ cm$^{-1}$: 2240(C≡N), 1700(C=O)
NMR Spectrum (CDCl$_3$) δppm: 1.47 (12H, dd, J=6 Hz.6 Hz) 4.87 (1H, m) 5.34 (2H, s) 5.54 (1H, m) 6.87 (1H, d, J=7 Hz) 6.91 (1H, t, J=7 Hz) 7.3~7.5 (5H, m) 8.08 (1H, d, J=7 Hz) 8.22 (1H, s)

3-[2-(Benzyloxycarbonyl)-2-cyanovinyl]-2-butoxy-8-methylimidazo[1,2-a]pyridine
Melting Point: 98°~100° C.
IR Spectrum $\nu_{max}^{KBr}$ cm$^{-1}$: 2240(C≡N), 1700(C=O)
NMR Spectrum (CDCl$_3$) δppm: 0.99 (3H, t, J=7 Hz) 1.55 (2H, m) 1.91 (2H, m) 2.54 (3H, s) 4.59 (2H, t, J=7 Hz) 5.34 (2H, s) 6.97 (1H, t, J=7 Hz) 7.2~7.5 (6H, m) 8.24 (1H, s) 8.36 (1H, d, J=7 Hz)

3-[2-(Benzyloxycarbonyl)-2-cyanovinyl]-2-isobutoxy-7-methylimidazo[1,2-a]pyridine
Melting Point: 111°~113° C.
IR Spectrum $\nu_{max}^{KBr}$ cm$^{-1}$: 2210(C≡N), 1700(C=O)
NMR Spectrum (CDCl$_3$) δppm: 1.05 (6H, d, J=7 Hz) 2.27 (1H, m) 2.47 (3H, s) 4.31 (2H, d, J=7 Hz) 5.33 (2H, s) 6.93 (1H, d, J=7 Hz) 7.30 (1H, s) 7.3~7.5 (5H, m) 8.24 (1H, s) 8.50 (1H, d, J=7 Hz)

3-[2-(Benzyloxycarbonyl)-2-cyanovinyl]-2-isobutoxy-5-methylimidazo[1,2-a]pyridine
Melting Point: 103°~105° C.
IR Spectrum $\nu_{max}^{KBr}$ cm$^{-1}$: 2210(C≡N), 1700(C=O)
NMR Spectrum (CDCl$_3$) δppm: 1.07 (6H, d, J=7 Hz) 2.37 (1H, m) 2.86 (3H, s) 4.37 (2H, d, J=7 Hz) 5.33 (2H, s) 6.79 (1H, d, J=7 Hz) 7.3~7.5 (7H, m) 8.66 (1H, s)

3-[2-(Benzyloxycarbonyl)-2-cyanovinyl]-8-methyl-2-sec-butoxyimidazo[1,2-a]pyridine
Melting Point: 105°~107° C.
IR Spectrum $\nu_{max}^{KBr}$ cm$^{-1}$: 2210(C≡N), 1705(C=O)
NMR Spectrum (CDCl$_3$) δppm: 0.98 (3H, t, J=7 Hz) 1.34 (3H, d, J=6 Hz) 1.6~1.9 (2H, m) 2.54 (3H, s) 5.34 (2H, s) 5.36 (1H, m) 6.96 (1H, t, J=7 Hz) 7.2~7.5 (6H, m) 8.25 (1H, s) 8.35 (1H, d, J=7 Hz)

3-[2-(Benzyloxycarbonyl)-2-cyanovinyl]-8-ethoxy-2-sec-butoxyimidazo-[1,2-a]pyridine
Melting Point: 99°~101° C.
IR Spectrum $\nu_{max}^{KBr}$ cm$^{-1}$: 2225(C≡N), 1690(C=O)
NMR Spectrum (CDCl$_3$) δppm: 1.00 (3H, t, J=7 Hz) 1.45 (3H, d, J=6 Hz) 1.55 (3H, t, J=7 Hz) 1.7~1.8 (1H, m) 1.9~2.0 (1H, m) 4.31 (2H, q, J=7 Hz) 5.34 (2H, s) 5.36 (1H, m) 6.83 (1H, d, J=7 Hz) 6.94 (1H, t, J=7 Hz) 7.3~7.5 (5H, m) 8.09 (1H, d, J=7 Hz) 8.23 (1H, s)

3-[2-(Benzyloxycarbonyl)-2-cyanovinyl]-8-isopropoxy-2-sec-butoxyimidazo[1,2-a]pyridine
Melting Point: 108°~109° C.
IR Spectrum $\nu_{max}^{KBr}$ cm$^{-1}$: 2210(C≡N), 1690(C=O)
NMR Spectrum (CDCl$_3$) δppm: 1.00 (3H, t, J=7 Hz) 1.45 (9H, d, J=6 Hz) 1.7~2.0 (2H, m) 4.86 (1H, m) 5.34 (2H, s) 5.36 (1H, m) 6.8~7.0 (2H, m) 7.3~7.5 (5H, m) 8.11 (1H, d, J=7 Hz) 8.23 (1H, s)

3-[2-(Benzyloxycarbonyl)-2-cyanovinyl]-2-hexyloxy-8-methylimidazo[1,2-a]pyridine
Melting Point: —(yellow glassy oil)
IR Spectrum $\nu_{max}^{KBr}$ cm$^{-1}$: 2240(C≡N), 1700(C=O)
NMR Spectrum (CDCl$_3$) δppm: 0.90 (3H, t, J=7 Hz) 1.2~1.6 (6H, m) 1.92 (2H, m) 2.54 (3H, s) 4.57 (2H, t, J=7 Hz) 5.34 (2H, s) 6.97 (1H, t, J=7 Hz) 7.2~7.5 (6H, m) 8.24 (1H, s) 8.36 (1H, d, J=7 Hz)

3-[2-Cyano-2-(isopentyloxycarbonyl)vinyl]-2,8-diisopropoxyimidazo[1,2-a]pyridine
Melting Point: 88°~89° C.
IR Spectrum $\nu_{max}^{KBr}$ cm$^{-1}$: 2220(C≡N), 1700(C=O)
NMR Spectrum (CDCl$_3$) δppm: 0.96 (6H, d, J=6 Hz) 1.45 (6H, d, J=6 Hz) 1.48 (6H, d, J=6 Hz) 1.6~1.9 (3H, m) 4.31 (2H, t, J=7 Hz) 4.86 (1H, m) 5.52 (1H, m) 6.85 (1H, d, J=7 Hz) 6.93 (1H, t, J=7 Hz) 8.08 (1H, d, J=7 Hz) 8.20 (1H, s)

3-[2-Cyano-2-(n-decyloxycarbonyl)vinyl]-2,8-diisopropoxyimidazo[1,2-a]pyridine
Melting Point: 73°~74.5° C.
IR Spectrum $\nu_{max}^{KBr}$ cm$^{-1}$: 2200(C≡N), 1700(C=O)
NMR Spectrum (CDCl$_3$) δppm: 0.88 (3H, t, J=7 Hz) 1.2~1.5 (26H, m) 1.75 (2H, m) 4.27 (2H, t, J=7 Hz) 4.87 (1H, m) 5.52 (1H, m) 6.85 (1H, d, J=7 Hz) 6.93 (1H, t, J=7 Hz) 8.08 (1H, d, J=7 Hz) 8.20 (1H, s)

3-[2-(Benzyloxycarbonyl)-2-cyanovinyl]-2-(3-hydroxypropoxy)-8-methylimidazo[1,2-a]pyridine
Melting Point: 128°~129° C.
IR Spectrum $\nu_{max}^{KBr}$ cm$^{-1}$: 2220(C≡N), 1700(C=O)
NMR Spectrum (CDCl$_3$) δppm: 2.10 (2H, quintet, J=5 Hz) 2.54 (3H, s) 3.68 (1H, broad s) 3.76 (2H, t, J=5 Hz) 4.82 (2H, t, J=5 Hz) 5.34 (2H, s) 7.00 (1H, t, J=7 Hz) 7.2~7.5 (6H, m) 8.2~8.3 (2H, m)

2-(3-Acetylaminopropoxy)-3-[2-(benzyloxycarbonyl)-2-cyanovinyl]-8-methylimidazo[1,2-a]pyridine
Melting Point: 134°~136° C.
IR Spectrum $\nu_{max}^{KBr}$ cm$^{-1}$: 2220(C≡N), 1690(C=O)
NMR Spectrum (CDCl$_3$) δppm: 1.97 (3H, s) 2.14 (2H, quintet, J=6 Hz) 2.54 (3H, s) 3.46 (2H, q, J=6 Hz) 4.71 (2H, t, J=6 Hz) 5.34 (2H, s) 6.65 (1H, broad s) 6.98 (1H, t, J=7 Hz) 7.2~7.5 (6H, m) 8.14 (1H, d, J=7 Hz) 8.24 (1H, s)

3-[2-(Benzyloxycarbonyl)-2-cyanovinyl]-2-cyclopropylmethoxy-8-methylimidazo[1,2-a]pyridine
Melting Point: 139°~140° C.
IR Spectrum $\nu_{max}^{KBr}$ cm$^{-1}$: 2210(C≡N), 1690(C=O)
NMR Spectrum (CDCl$_3$) δppm: 0.4~0.5 (2H, m) 0.6~0.7 (2H, m) 1.4~1.5 (1H, m) 2.53 (3H, s) 4.42 (2H, d, J=7 Hz) 5.34 (2H, s) 6.97 (1H, t, J=7 Hz) 7.2~7.5 (6H, m) 8.27 (1H, s) 8.37 (1H, d, J=7 Hz)

3-[2-(Benzyloxycarbonyl)-2-cyanovinyl]-2-(2-methoxyethoxy)-8-methylimidazo[1,2-a]pyridine
Melting Point: 88°~90° C.
IR Spectrum $\nu_{max}^{KBr}$ cm$^{-1}$: 2210(C≡N), 1700(C=O)
NMR Spectrum (CDCl$_3$) δppm: 2.54 (3H, s) 3.46 (3H, s) 3.89 (2H, t, J=5 Hz) 4.74 (2H, t, J=5 Hz) 5.34 (2H, s) 6.97 (1H, t, J=7 Hz) 7.3~7.5 (6H, m) 8.25 (1H, s) 8.33 (1H, d, J=7 Hz)

3-[2-(Benzyloxycarbonyl)-2-cyanovinyl]-2-(3-cyanopropoxy)-8-methylimidazo[1,2-a]pyridine
Melting Point: 128°~130° C.
IR Spectrum $\nu_{max}^{KBr}$ cm$^{-1}$: 2220(C≡N), 1700(C=O)
NMR Spectrum (CDCl$_3$) δppm: 2.29 (2H, quintet, J=6 Hz) 2.55 (3H, s) 2.76 (2H, t, J=6 Hz) 4.73 (2H, t, J=6 Hz) 5.34 (2H, s) 6.99 (1H, t, J=7 Hz) 7.3~7.5 (6H, m) 8.17 (1H, d, J=7 Hz) 8.23 (1H, s)

EXAMPLE 3

3-(2-Carboxy-2-cyanovinyl)-8-methyl-2-(2-propenyloxy)imidazo[1,2-a]pyridine and sodium salt thereof Potassium carbonate (312 mg) was added to a suspension of 3-[2-cyano-2-(ethoxycarbonyl)vinyl]-8-methyl-2-(2-propenyloxy)imidazo[1,2-a]pyridine (312 mg; 1.0 mmol), 10 ml of water, and 10 ml of ethanol. Then the mixture was stirred for 30 min at 60° C. and cooled at room temperature. To the residue obtained by evaporating the solvent, was added water (15 ml) and saturated sodium bicarbonate aqueous solution (15 ml). After removal of insoluble matter by filtration, the filtrate was made acidic with hydrochloric acid (2N). The resultant yellow needles were collected by filtration, dried to give 113 mg (yield: 40%) of the titled carboxylic acid.

The carboxylic acid thus obtained was added to an aqueous sodium bicarbonate (30 mg in 50 ml of water), and the mixture was stirred for 3 hours at room temperature. After removal of precipitates by filtration, the filtrate was lyophilized to give 110 mg of the titled sodium salt as yellow powder.

Titled Carboxylic Acid
Melting Point: 181° C. (dec.)
Titled Sodium Salt
Melting Point: 209° C. (dec.)
IR Spectrum $\nu_{max}^{KBr}$ cm$^{-1}$: 2210(C≡N), 1620(C=O)
NMR Spectrum (D$_2$O) δppm: 2.29 (3H, s) 4.95 (2H, d, J=4 Hz) 5.36 (1H, d, J=10 Hz) 5.51 (1H, d, J=18 Hz) 6.0~6.2 (1H, m) 6.87(1H, t, J=7 Hz) 7.17(1H, d, J=7 Hz) 7.69 (1H, s) 7.86(1H, d, J=7 Hz)

In accordance with the procedure of the Example 3, the following compounds were obtained from the corresponding starting materials.

3-(2-Carboxy-2-cyanovinyl)-2-methoxyimidazo[1,2-a]pyridine and sodium salt thereof
Titled Carboxylic Acid
Melting Point: 222° C. (dec.)
Titled Sodium Salt
Melting Point: 211° C. (dec.)
IR Spectrum $\nu_{max}^{KBr}$ cm$^{-1}$: 2210(C≡N), 1630(C=O)
NMR Spectrum (DMSO-d$_6$) δppm: 4.04 (3H, s) 7.00 (1H, t, J=7 Hz) 7.43 (1H, t, J=7 Hz) 7.56 (1H, d, J=7 Hz) 8.07 (1H, s) 8.51 (1H, d, J=7 Hz)

3-(2-Carboxy-2-cyanovinyl)-2-methoxy-8-methylimidazo[1,2-a]pyridine and sodium salt thereof
Titled Carboxylic Acid
Melting point: 221° C. (dec.)
Titled Sodium Salt
Melting Point: 224° C. (dec.)
IR Spectrum $\nu_{max}^{KBr}$ cm$^{-1}$: 2210(C≡N), 1620(C=O)
NMR Spectrum (DMSO-d$_6$) δppm: 2.47 (3H, s) 4.06 (3H, s) 7.00 (1H, t, J=7 Hz) 7.26 (1H, d, J=7 Hz) 8.02 (1H, s) 8.35 (1H, d, J=7 Hz)

3-(2-Carboxy-2-cyanovinyl)-2-methoxy-6-methylimidazo[1,2-a]pyridine and sodium salt thereof
Titled Carboxylic Acid
Melting Point: 215° C. (dec.)
Titled Sodium Salt
Melting Point: 225° C. (dec.)
IR Spectrum $\nu_{max}^{KBr}$ cm$^{-1}$: 2200(C≡N), 1610(C=O)
NMR Spectrum (D$_2$O) δppm: 2.19 (3H, s) 3.80 (3H, s) 6.98 (1H, d, J=9 Hz) 7.19 (1H, d, J=9 Hz) 7.43 (1H, s) 7.69 (1H, s)

2-(3-Butenyloxy)-3-(2-carboxy-2-cyanovinyl)-8-methylimidazo[1,2-a]pyridine and sodium salt thereof
Titled Carboxylic Acid
Melting Point: 177° C. (dec.)
Titled Sodium Salt
Melting Point: 248° C. (dec.)
IR Spectrum $\nu_{max}^{KBr}$ cm$^{-1}$: 2210(C≡N), 1610(C=O)
NMR Spectrum (D$_2$O) δppm: 2.29 (3H, s) 2.59 (2H, m) 4.32 (2H, t, J=6 Hz) 5.19 (2H, dd, J=18 Hz, 11 Hz)

5.9~6.1 (1H, m) 6.86 (1H, t, J=7 Hz) 7.17 (1H, d, J=7 Hz) 7.71 (1H, s) 7.87 (1H, d, J=7 Hz)

EXAMPLE 4

3-(2-Carboxy-2-cyanovinyl)-2-ethoxy-8-methylimidazo[1,2-a]pyridine and sodium salt thereof A solution of 3-[2-(benzyloxycarbonyl)-2-cyanovinyl]-2-ethoxy-8-methylimidazo[1,2-a]pyridine (250 mg; 0.7 mmol) in ethanol (280 ml) was stirred under hydrogen atmosphere in the presence of 10% palladium on carbon (25 mg) for an hour at room temperature. After removal of the catalysis, the filtrate was evaporated to dryness. Saturated aqueous sodium bicarbonate (6 ml) was added to the residue. After removal of insoluble matter by filtration, the filtrate was made acidic with hydrochloric acid (2N). The resultant precipitates were collected by filtration and dried to give 153 mg (yield: 81%) of the titled carboxylic acid.

The carboxylic acid thus obtained was added to an aqueous sodium bicarbonate (45 mg in 50 ml of water) and the mixture was stirred for 3 hours at room temperature. Insoluble matter was removed by filtration, and the filtrate was lyophilized to give 160 mg of the titled sodium salt as yellow powder.

Titled Carboxylic Acid
Melting Point: 194°~195° C. (dec.)
Titled Sodium Salt
Melting Point: 267° C. (dec.)
IR Spectrum $\nu_{max}^{KBr}$cm$^{-1}$: 2210(C≡N), 1610(C=O)
NMR Spectrum (D$_2$O) δppm: 1.39 (3H, t, J=7 Hz) 2.30 (3H, s) 4.21 (2H, q, J=7 Hz) 6.81 (1H, t, J=7 Hz) 7.12 (1H, d, J=7 Hz) 7.52 (1H, s) 7.76 (1H, d, J=7 Hz)

In accordance with the procedure of the Example 4, the following compounds were obtained from the corresponding starting materials.

3-(2-Carboxy-2-cyanovinyl)-2-methoxy-5,7-dimethylimidazo[1,2-a]pyridine and sodium salt thereof
Titled Carboxylic Acid
Melting Point: 236°~238° C. (dec.)
Titled Sodium Salt
Melting Point: 232°~233° C. (dec.)
IR Spectrum $\nu_{max}^{KBr}$cm$^{-1}$: 2220(C≡N), 1620(C=O)
NMR Spectrum (D$_2$O) δppm: 2.27 (3H, s) 2.52 (3H, s) 4.01 (3H, s) 6.60 (1H, s) 6.90 (1H, s) 8.20 (1H, s)

3-(2-Carboxy-2-cyanovinyl)-6,8-dichloro-2-methoxyimidazo[1,2-a]pyridine and and sodium salt thereof
Titled Carboxylic Acid
Melting Point: 234°~235° C. (dec.)
Titled Sodium Salt
Melting Point: 236° C. (dec.)
IR Spectrum $\nu_{max}^{KBr}$cm$^{-1}$: 2210(C≡N), 1610(C=O)
NMR Spectrum (D$_2$O) δppm: 4.02 (3H, s) 7.59 (1H, s) 7.75 (1H, s) 8.32 (1H, s)

3-(2-Carboxy-2-cyanovinyl)-2-ethoxy-8-isopropoxyimidazo[1,2-a]pyridine and sodium salt thereof
Titled Carboxylic Acid
Melting Point: 188°~189° C. (dec.)
Titled Sodium Salt
Melting Point: 239°~240° C. (dec.)
IR Spectrum $\nu_{max}^{KBr}$cm$^{-1}$: 2215(C≡N), 1620(C=O)
NMR Spectrum (D$_2$O) δppm: 1.39 (6H, d, J=6 Hz) 1.46 (3H, t, J=7 Hz) 4.45 (2H, q, J=7 Hz) 5.14 (1H, m) 6.90 (2H, d, J=5 Hz) 7.74 (1H, s, J=5 Hz) 7.92 (1H, s)

3-(2-Carboxy-2-cyanovinyl)-8-methyl-2-propoxyimidazo[1,2-a]pyridine and sodium salt thereof
Titled Carboxylic Acid
Melting point: 183° C. (dec.)
Titled Sodium Salt
Melting Point: 245° C. (dec.)
IR Spectrum $\nu_{max}^{KBr}$cm$^{-1}$: 2210(C≡N), 1610(C=O)
NMR Spectrum (D$_2$O) δppm: 1.03 (3H, t, J=7 Hz) 1.84 (2H, m) 2.32 (3H, s) 4.25 (2H, t, J=7 Hz) 6.89 (1H, t, J=7 Hz) 7.20 (1H, d, J=7 Hz) 7.76 (1H, s) 7.92 (1H, d, J=7 Hz)

3-(2-Carboxy-2-cyanovinyl)-2-isopropoxy-8-methylimidazo[1,2-a]-pyridine and sodium salt thereof
Titled Carboxylic Acid
Melting Point: 193° C. (dec.)
Titled Sodium Salt
Melting Point: 245° C. (dec.)
IR Spectrum $\nu_{max}^{KBr}$cm$^{-1}$: 2240(C≡N), 1680(C=O)
NMR Spectrum (DMSO-d$_6$) δppm: 1.44 (6H, d, J=6 Hz) 2.46 (3H, s) 5.36 (1H, m) 7.08 (1H, t, J=7 Hz) 7.44 (1H, d, J=7 Hz) 8.24 (1H, s) 8.60 (1H, d, J=7 Hz)

3-(2-Carboxy-2-cyanovinyl)-2-isopropoxy-8-methoxyimidazo[1,2-a]-pyridine and sodium salt thereof
Titled Carboxylic Acid
Melting Point: 200°~201° C. (dec.)
Titled Sodium Salt
Melting Point: 300°~302° C. (dec.)
IR Spectrum $\nu_{max}^{KBr}$cm$^{-1}$: 2200(C≡N), 1600(C=O)
NMR Spectrum (D$_2$O) δppm: 1.40 (6H, d, J=6 Hz) 3.87 (3H, s) 4.81 (1H, m) 6.71 (1H, d, J=7 Hz) 6.78 (1H, t, J=7 Hz) 7.53 (1H, d, J=7 Hz) 7.69 (1H, s)

3-(2-Carboxy-2-cyanovinyl)-8-ethoxy-2-isopropoxyimidazo[1,2-a]-pyridine and sodium salt thereof
Titled Carboxylic Acid
Melting Point: 199°~201° C. (dec.)
Titled Sodium Salt
Melting Point: 244°~247° C. (dec.)
IR Spectrum $\nu_{max}^{KBr}$cm$^{-1}$: 2210(C≡N), 1620(C=O)
NMR Spectrum (D$_2$O) δppm: 1.4~1.5 (9H, m) 4.05 (2H, q, J=7 Hz) 4.98 (1H, m) 6.6~6.8 (2H, m) 7.46 (1H, d, J=6 Hz) 7.70 (1H, s)

3-(2-Carboxy-2-cyanovinyl)-2,8-diisopropoxyimidazo[1,2-a]pyridine and sodium salt thereof
Titled Carboxylic Acid
Melting Point: 197°~198° C. (dec.)
Titled Sodium Salt
Melting Point: 251°~252° C. (dec.)
IR Spectrum $\nu_{max}^{KBr}$cm$^{-1}$: 2215(C≡N), 1620(C=O)
NMR Spectrum (D$_2$O) δppm: 1.39 (6H, d, J=6 Hz) 1.42 (6H, d J=6 Hz) 4.70 (1H, m) 5.14 (1H, m) 6.84 (2H, d, J=4 Hz) 7.67 (1H, t, J=4 Hz) 7.92 (1H, s)

2-Butoxy-3-(2-carboxy-2-cyanovinyl)-8-methylimidazo[1,2-a]pyridine and sodium salt thereof
Titled Carboxylic Acid
Melting Point: 185° C. (dec.)
Titled Sodium Salt
Melting Point: 277° C. (dec.)
IR Spectrum $\nu_{max}^{KBr}$cm$^{-1}$: 2205(C≡N), 1610(C=O)
NMR Spectrum (D$_2$O) δppm: 0.97 (3H, t, J=7 Hz) 1.47 (2H, m) 1.80 (2H, m) 2.28 (3H, s) 4.25 (2H, t, J=7 Hz) 6.85 (1H, t, J=7 Hz) 7.16 (1H, d, J=7 Hz) 7.69 (1H, s) 7.86 (1H, d, J=7 Hz)

3-(2-Carboxy-2-cyanovinyl)-2-isobutoxy-7-methylimidazo[1,2-a]pyridine and sodium salt thereof
Titled Carboxylic Acid
Melting Point: 200°~201° C. (dec.)
Titled Sodium Salt
Melting Point: 209°~217° C. (dec.)
IR Spectrum $\nu_{max}^{KBr}cm^{-1}$: 2205(C≡N), 1605(C=O)
NMR Spectrum (D$_2$O) δppm: 1.01 (6H, d, J=7 Hz) 2.06 (1H, m) 2.27 (3H, s) 3.88 (2H, d, J=6 Hz) 6.70 (1H, d, J=7 Hz) 6.81 (1H, s) 7.51 (1H, s) 7.73 (1H, d, J=7 Hz)

3-(2-Carboxy-2-cyanovinyl)-2-isobutoxy-5-methylimidazo[1,2-a]pyridine and sodium salt thereof
Titled Carboxylic Acid
Melting Point: 169°~171° C. (dec.)
Titled Sodium Salt
Melting Point: 252°~253° C. (dec.)
IR Spectrum $\nu_{max}^{KBr}cm^{-1}$: 2210(C≡N), 1615(C=O)
NMR Spectrum (D$_2$O) δppm: 1.04 (6H, d, J=7 Hz) 2.13 (1H, m) 2.46 (3H, s) 3.98 (2H, d, J=7 Hz) 6.48 (1H, d, J=7 Hz) 6.84 (1H, d, J=7 Hz) 7.04 (1H, dd, J=7 Hz.7 Hz) 8.11 (1H, s)

3-(2-Carboxy-2-cyanovinyl)-8-methyl-2-sec-butoxyimidazo[1,2-a]pyridine and sodium salt thereof
Titled Carboxylic Acid
Melting Point: 175°~177° C. (dec.)
Titled Sodium Salt
Melting Point: 262°~265° C. (dec.) IR Spectrum $\nu_{max}^{KBr}cm^{-1}$: 2220(C≡N), 1600(C=O)
NMR Spectrum (D$_2$O) δppm: 0.96 (3H, t, J=7 Hz) 1.36 (3H, d, J=6 Hz) 1.6~1.9 (2H, m) 2.25 (3H, s) 4.87 (1H, m) 6.71 (1H, dd, J=7 Hz.7 Hz) 7.03 (1H, d, J=7 Hz) 7.71 (1H, s) 7.73 (1H, d, J=7 Hz)

3-(2-Carboxy-2-cyanovinyl)-8-ethoxy-2-sec-butoxyimidazo[1,2-a]pyridine and sodium salt thereof
Titled Carboxylic Acid
Melting Point: 193°~194° C. (dec.)
Titled Sodium Salt
Melting Point: 266°~268° C. (dec.)
IR Spectrum $\nu_{max}^{KBr}cm^{-1}$: 2210(C≡N), 1605(C=O)
NMR Spectrum (D$_2$O) δppm: 0.98 (3H, t, J=7 Hz) 1.37 (3H, d J=6 Hz) 1.42 (3H, t, J=7 Hz) 1.77 (2H, m) 4.03 (2H, q, J=7 Hz) 4.85 (1H, m) 6.57 (1H, d, J=7 Hz) 6.63 (1H, t, J=7Hz) 7.42 (1H, d, J=7 Hz) 7.71 (1H, s)

3-(2-Carboxy-2-cyanovinyl)-8-isopropoxy-2-sec-butoxyimidazo[1,2-a]pyridine and sodium salt thereof
Titled Carboxylic Acid
Melting Point: 171°~172° C. (dec.)
Titled Sodium Salt
Melting Point: 248° C. (dec.)
IR Spectrum $\nu_{max}^{KBr}cm^{-1}$: 2215(C≡N), 1600(C=O)
NMR Spectrum (D$_2$O) δppm: 0.98 (3H, t, J=7 Hz) 1.38 (9H, d, J=6 Hz) 1.6~2.0 (2H, m) 4.66 (1H, m) 4.98 (1H, m) 6.76 (2H, d, J=4 Hz) 7.60 (1H, t, J=4 Hz) 7.90 (1H, s)

3-(2-Carboxy-2-cyanovinyl)-2-hexyloxy-8-methylimidazo[1,2-a]pyridine and sodium salt thereof
Titled Carboxylic Acid
Melting Point: 173° C. (dec.)
Titled Sodium Salt
Melting Point: 231° C. (dec.)
IR Spectrum $\nu_{max}^{KBr}cm^{-1}$: 2230(C≡N), 1600(C=O)

NMR Spectrum (D$_2$O) δppm: 0.89 (3H, t, J=6 Hz) 1.2~1.5 (6H, m) 1.75 (2H, m) 2.18 (3H, s) 4.16 (2H, t, J=7 Hz) 6.74 (1H, t, J=7 Hz) 7.02 (1H, d, J=7 Hz) 7.60 (1H, s) 7.75 (1H, d, J=7 Hz)

3-(2-Carboxy-2-cyanovinyl)-2-(3-hydroxypropoxy)-8-methylimidazo[1,2-a]pyridine and sodium salt thereof
Titled Carboxylic Acid
Melting Point: 182° C. (dec.)
Titled Sodium Salt
Melting Point: 48° C.
IR Spectrum $\mu_{max}^{KBr}cm^{-1}$: 2220(C≡N), 1620(C=O)
NMR Spectrum (D$_2$O) δppm: 2.09 (2H, quintet, J=6 Hz) 2.32 (3H, s) 3.82 (2H, t, J=6 Hz) 4.39 (2H, t, J=6 Hz) 6.90 (1H, t, J=7 Hz) 7.21 (1H, t, J=7 Hz) 7.74 (1H, s) 7.91 (1H, d, J=7 Hz)

2-(3-Acetylaminopropoxy)-3-(2-carboxy-2-cyanovinyl)-8-methylimidazo[1,2-a]pyridine and sodium salt thereof
Titled Carboxylic Acid
Melting Point: 212° C. (dec.)
Titled Sodium Salt
Melting Point: 138° C.
IR Spectrum $\nu_{max}^{KBr}cm^{-1}$: 2220(C≡N), 1615(C=O)
NMR Spectrum (D$_2$O) δppm: 1.9~2.1 (5H, m) 2.17 (3H, s) 3.34 (2H, t, J=6.5 Hz) 4.17 (2H, t, J=6.5 Hz) 6.72 (1H, t, J=7 Hz) 7.02 (1H, d, J=7 Hz) 7.48 (1H, s) 7.67 (1H, d, J=7 Hz)

3-(2-Carboxy-2-cyanovinyl)-2-cyclopropylmethoxy-8-methylimidazo[1,2-a]pyridine and sodium salt thereof
Titled Carboxylic Acid
Melting Point: 188° C. (dec.)
Titled Sodium Salt
Melting Point: 251° C. (dec.)
IR Spectrum $\nu_{max}^{KBr}cm^{-1}$: 2210(C≡N), 1610(C=O)
NMR Spectrum (D$_2$O) δppm: 0.3~0.5 (2H, m) 0.6~0.7 (2H, m) 1.2~1.4 (1H, m) 2.27 (3H, s) 4.10 (2H, d, J=7 Hz) 6.84 (1H, t, J=7 Hz) 7.14 (1H, d, J=7 Hz) 7.69 (1H, s) 7.84 (1H, d, J=7 Hz)

3-(2-Carboxy-2-cyanovinyl)-2-(2-methoxyethoxy)-8-methylimidazo[1,2-a]pyridine and sodium salt thereof
Titled Carboxylic Acid
Melting Point: 185°~187° C. (dec.)
Titled Sodium Salt
Melting Point: 223°~226° C. (dec.)
IR Spectrum $\nu_{max}^{KBr}cm^{-1}$: 2210(C≡N), 1610(C=O)
NMR Spectrum (D$_2$O) δppm: 2.24 (3H, s) 3.47 (3H, s) 3.89 (2H, t, J=4 Hz) 4.39 (2H, t, J=4 Hz) 6.81 (1H, t, J=7 Hz) 7.12 (1H, d, J=7 Hz) 7.60 (1H, s) 7.78 (1H, d, J=7 Hz)

3-(2-Carboxy-2-cyanovinyl)-2-(3-cyanopropoxy)-8-methylimidazo[1,2-a]pyridine and sodium salt thereof
Titled Carboxylic Acid
Melting Point: 194°~196° C. (dec.)
Titled Sodium Salt
Melting Point: 220°~222° C. (dec.)
IR Spectrum $\nu_{max}^{KBr}cm^{-1}$: 2210(C≡N), 1600(C=O)
NMR Spectrum (D$_2$O) δppm: 2.17 (2H, m) 2.20 (3H, s) 2.76 (2H, t, J=7 Hz) 4.27 (2H, t, J=5 Hz) 6.77 (1H, t, J=7 Hz) 7.07 (1H, d, J=7 Hz) 7.50 (1H, s) 7.70 (1H, d, J=7 Hz)

CAPABILITY OF EXPLOITATION IN INDUSTRY

As described above, 1-azaindolizine derivatives of the present invention and synthetic intermediates thereof exhibit an excellent inhibition against PCA reaction, and are very useful as antiallergic agents which are effective in a remedy or a prophylactic for some allergic diseases such as allergic bronchial asthma, allergic rhinitis and atopic dermatitis.

We claim:

1. 1-Azaindolizine derivatives or pharmaceutically acceptable salts thereof represented by formula (I)

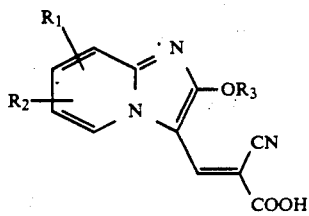

wherein $R_1$ and $R_2$ independently represent hydrogen atom, halogen atom, $C_{1-4}$ alkyl group or $C_{1-4}$ alkoxy group; $R_3$ represents $C_{1-6}$ alkyl group, substituted $C_{1-4}$ alkyl group wherein the substituent is $C_{3-5}$ cycloalkyl group, hydroxyl group, acetylamino group, $C_{1-4}$ alkoxy group or cyano group or $C_{2-4}$ alkenyl group.

2. The compound according to claim 1 wherein $R_1$ and $R_2$ independently represent hydrogen atom, $C_{1-4}$ alkyl group or $C_{1-4}$ alkoxy group; and $R_3$ represents $C_{1-6}$ alkyl group or acetylamino $C_{1-4}$ alkyl group.

3. The compound according to claim 2 wherein $R_3$ represents $C_{3-6}$ alkyl group.

4. The compound according to claim 2 wherein $R_3$ represents acetylamino $C_{1-4}$ alkyl group.

5. Synthetic intermediates of the compound according to claim 1 represented by formula (II)

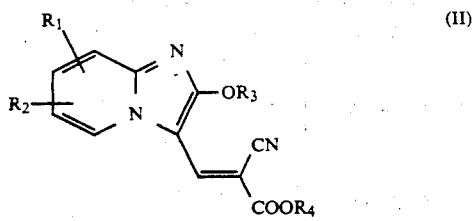

wherein $R_1$ and $R_2$ independently represent hydrogen atom, halogen atom, $C_{1-4}$ alkyl group or $C_{1-4}$ alkoxy group;

$R_3$ represents $C_{1-6}$ alkyl group, substituted $C_{1-4}$ alkyl group wherein the substituent is $C_{3-5}$ cycloalkyl group, hydroxy group, acetylamino group, $C_{1-4}$ alkoxy group or cyano group or $C_{2-4}$ alkenyl group; and $R_4$ represents $C_{1-10}$ alkyl group or benzyl group.

6. The compound according to claim 5 wherein $R_1$ and $R_2$ independently represent hydrogen atom, $C_{1-4}$ alkyl group or $C_{1-4}$ alkoxy group; and $R_3$ represents $C_{1-6}$ alkyl group or acetylamino $C_{1-4}$ alkyl group.

7. The compound according to claim 6 wherein $R_3$ represents $C_{3-6}$ alkyl group.

8. The compound according to claim 6 wherein $R_3$ represents acetylamino $C_{1-4}$ alkyl group.

9. A pharmaceutical composition containing a compound according to any one of claims 1 to 4 as antiallergic active component and a pharmaceutically acceptable diluent or carrier.

* * * * *